(12) United States Patent
Otsubo et al.

(10) Patent No.: US 6,450,998 B1
(45) Date of Patent: Sep. 17, 2002

(54) DISPOSABLE ARTICLE FOR DEALING WITH FECES

(75) Inventors: Toshifumi Otsubo; Hiroyuki Tanji; Yoshitaka Mishima; Naomi Suzuki; Kazuaki Onishi; Norihiko Ishikawa; Yoko Yabe, all of Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 71 days.

(21) Appl. No.: 09/605,833

(22) Filed: Jun. 29, 2000

(30) Foreign Application Priority Data

Jun. 29, 1999 (JP) .......................................... 11-184427

(51) Int. Cl.⁷ ................................................ A61F 13/15
(52) U.S. Cl. ............. 604/385.01; 604/358; 604/585.02; 604/369; 604/383
(58) Field of Search ........................ 604/385.01, 358, 604/385.02, 369, 383

(56) References Cited

U.S. PATENT DOCUMENTS

| | | | |
|---|---|---|---|
| 5,306,266 A | * | 4/1994 | Freeland ..................... 604/358 |
| 5,397,319 A | | 3/1995 | Suzuki |
| 5,417,680 A | * | 5/1995 | Kimura et al. .............. 604/358 |
| 5,556,393 A | * | 9/1996 | Ronnberg .................... 604/369 |
| 6,015,936 A | * | 1/2000 | Takai et al. ................. 604/358 |
| 6,114,597 A | * | 9/2000 | Romare ....................... 604/378 |
| 6,168,583 B1 | * | 1/2001 | Tanji et al. ............. 604/385.01 |
| 6,210,387 B1 | * | 4/2001 | Rudberg et al. ............. 604/358 |
| 6,328,724 B1 | * | 12/2001 | Ronnberg et al. ....... 604/385.01 |

FOREIGN PATENT DOCUMENTS

| | | | | |
|---|---|---|---|---|
| EP | 0350871 A | | 1/1990 | |
| EP | 359410 | * | 3/1990 | .......... A61F/13/15 |
| EP | 0908162 A2 | * | 4/1999 | .......... A61F/13/15 |
| JP | 4-15921 | | 2/1992 | |
| JP | 5-86320 | | 11/1993 | |
| JP | 7-7620 | | 2/1995 | |
| WO | WO 9107156 A | | 5/1991 | |
| WO | WO 9816180 A | | 4/1998 | |
| WO | WO 9817219 A | | 4/1998 | |
| WO | WO 99 25297 A | | 5/1999 | |

* cited by examiner

*Primary Examiner*—Rodney M. Lindsey
*Assistant Examiner*—Angela J Grayson
(74) *Attorney, Agent, or Firm*—Clark & Brody

(57) ABSTRACT

A disposable article for dealing with feces adapted to be used in conjunction with a disposable diaper or diaper cover. The article includes a feces receiving region that is provided in the form of a laminate that includes a top layer provided with at least one opening having an area of 20~500 mm², a feces holding layer in the form of a three-dimensional network structure underlying the top layer, a liquid-absorbent layer underlying the holding layer and a liquid-impervious back layer covering a lower surface of the absorbent layer. The laminate has its width progressively reduced toward a front end of the feces receiving pocket and a leakage barrier is formed along transversely opposite side edges of the top layer.

10 Claims, 8 Drawing Sheets

DISPOSABLE ARTICLE FOR DEALING WITH FECES

BACKGROUND OF THE INVENTION

This invention relates to a disposable article for dealing with a feces suitable for use with a disposable diaper, a diaper cover or the like.

A disposable diaper is well known which is formed on the inner surface of its crotch region with a recess adapted to receive a feces. For example, the diaper of such type can be found in the respective descriptions of Japanese Utility Model Application Disclosure Nos. 1992–15921; 1993–86320; and 1995–7620.

The diaper disclosed by these documents is certainly convenient in that one and same diaper can deal with both feces and urine. However, if such diaper is used to deal with urine only, the additional materials and labor having been required to make the diaper with intention of dealing with feces as well as urine will be completely wasted. In other words, users of such diaper will dispose of the diaper after its use without enjoying the convenience which should be offered by this diaper. No matter whether the users are conscious of it or not, the users are forced to buy the diaper at an unreasonably high price.

SUMMARY OF THE INVENTION

It is an object of this invention to provide a disposable article improved so that feces may be dealt with independently of urine in a simplified manner.

According to this invention, there is provided a disposable article for dealing with feces, having a longitudinal axis and a transverse axis orthogonal to the longitudinal axis, comprising: a front region, a rear region adjoining the front region in a direction defined by the longitudinal axis and a feces receiving region formed symmetrically about the longitudinal axis; and the feces receiving region being provided in the form of a laminate that includes a top layer formed with at least one opening having an area of 20–5000 mm$^2$, a feces holding layer in the form of a three-dimensional structure underlying the top layer and formed with a hollow immediately under the opening of the top layer and having an opening area substantially corresponding to the area of the opening formed in the top layer, a liquid-absorbent layer underlying the holding layer and containing liquid-absorbent material of at least 50 w/w % and a liquid-impervious back layer covering a lower surface of the absorbent layer, wherein the rear region is formed to have a substantially uniform dimension in a direction defined by the transverse axis while the front region is formed to be tapered toward a front edge of the laminate and the top layer is provided on an upper surface thereof with a leakage barrier continuously extending along transversely opposite side edges of the top layer across the front and rear regions and wherein the leakage barrier is normally biased to rise on the top layer but elastically deformable in the opposed direction.

DETAILED DESCRIPTION OF THE PREFERRED EMBODIMENTS

A disposable article for dealing with feces according to this invention particularly in the form of a pad for dealing with feces as one embodiment will be described in more detail with reference to the accompanying drawings.

Figure 1:
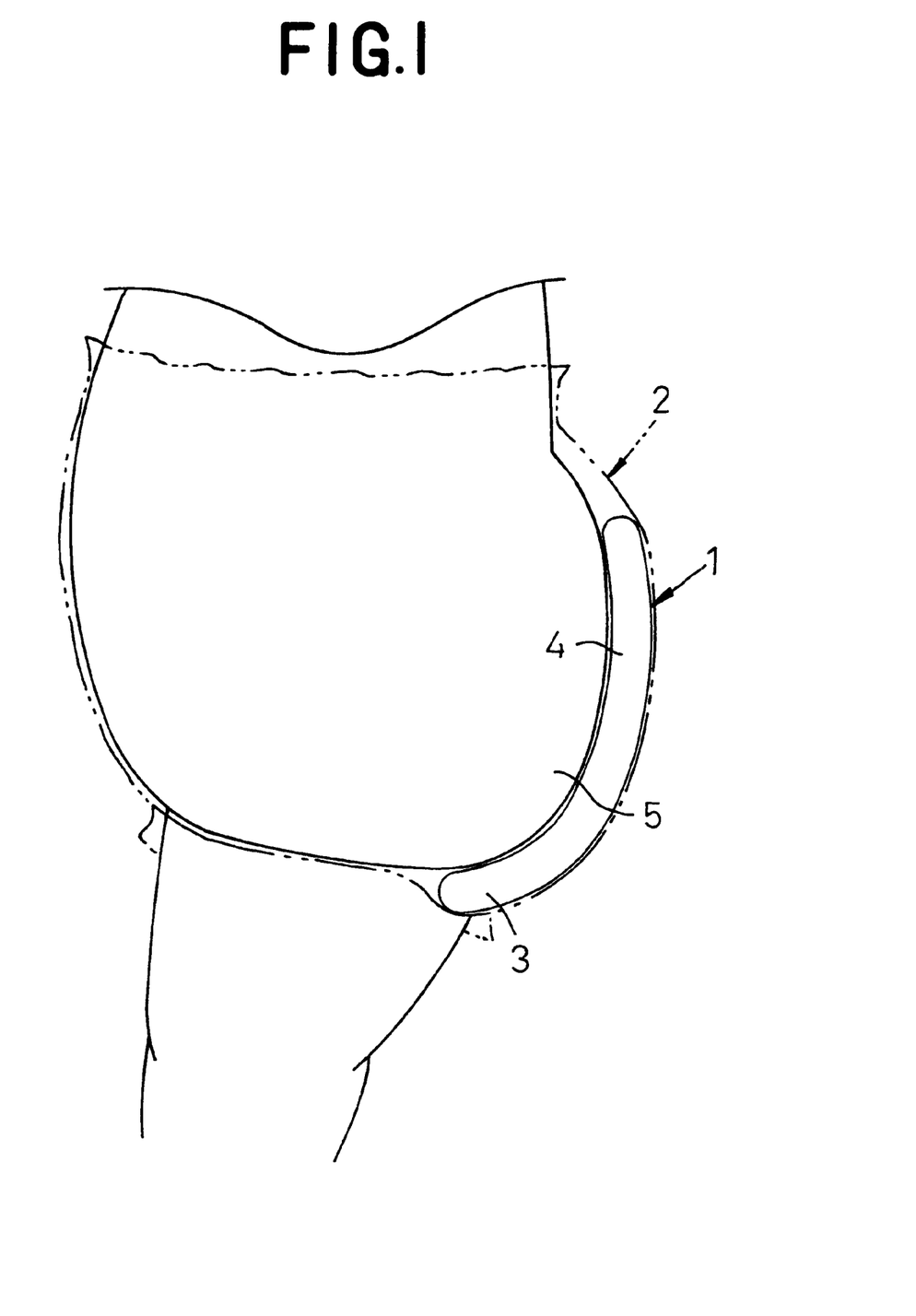
FIG. 1 is a side view showing the article (pad) according to this invention as put on a user's body.

FIG. 1 is a side view showing a pad 1 as put on a wearer's body. The pad 1 is placed on the inner side of an article 2 such as a disposable diaper or shorts to be used jointly with this pad 1 so that the pad 1 may be pressed by the article 2 against the wearer's hip around his or her anus. The pad 1 put on the wearer's body presents a substantially J- or L-shape in its side view wherein a lower portion of the J- or L-shape is defined by a front region 3 and a higher portion of the J- or L-shape is defined by a rear region 4 of the pad 1.

Figure 2:
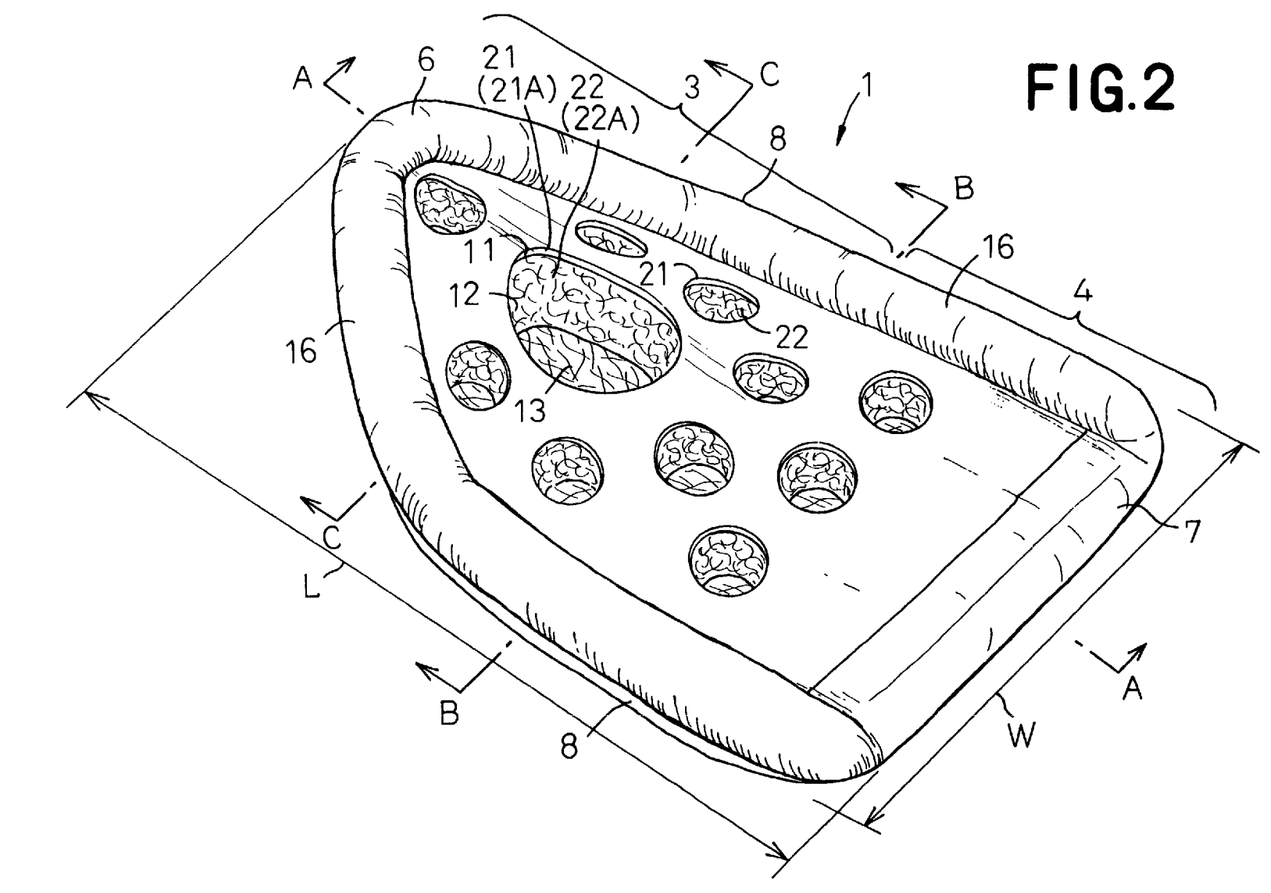
FIG. 2 is a perspective view of the article.
Figure 3:
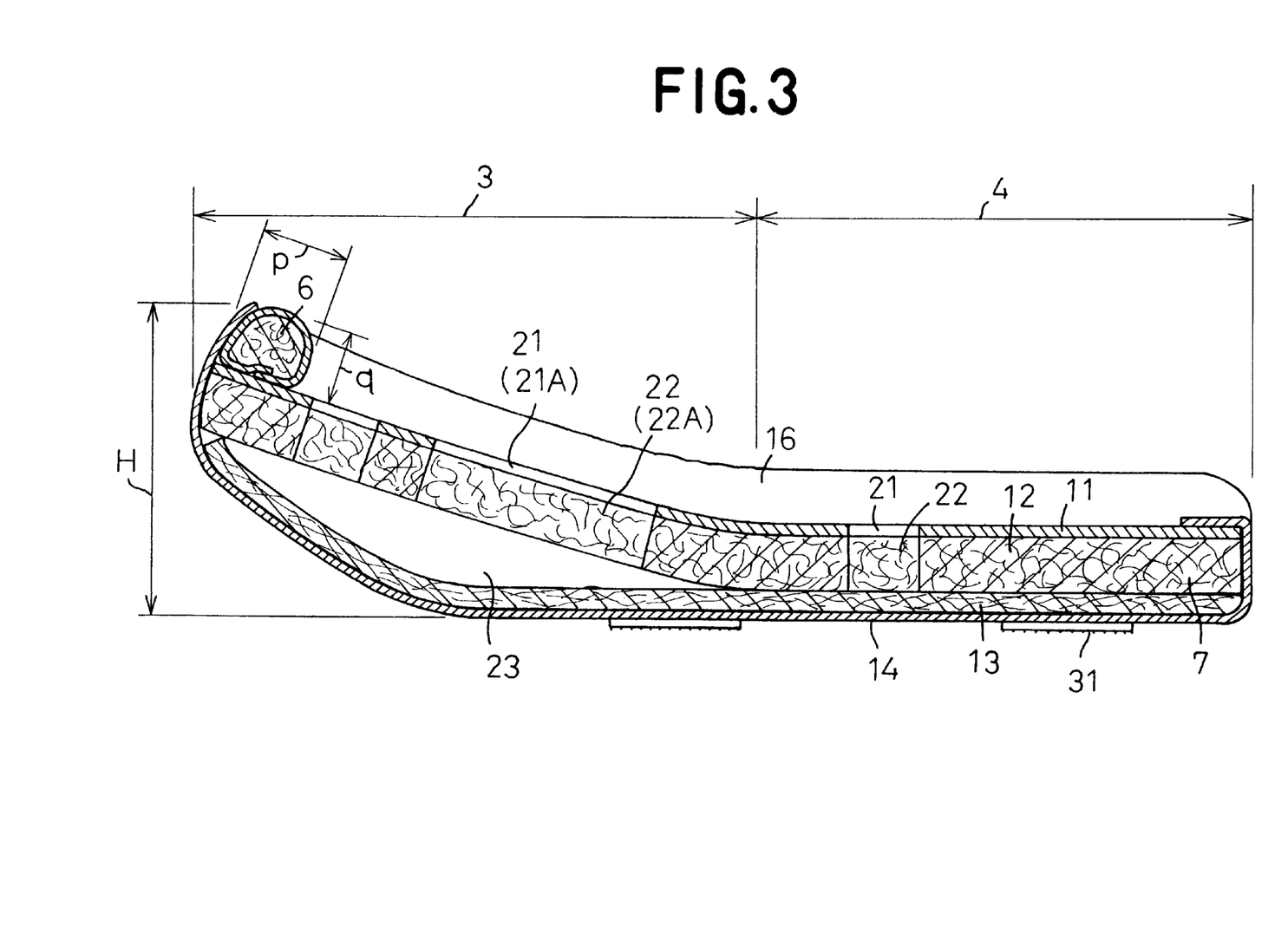
FIG. 3 is a sectional view taken along line A—A in FIG. 2.
Figure 4:
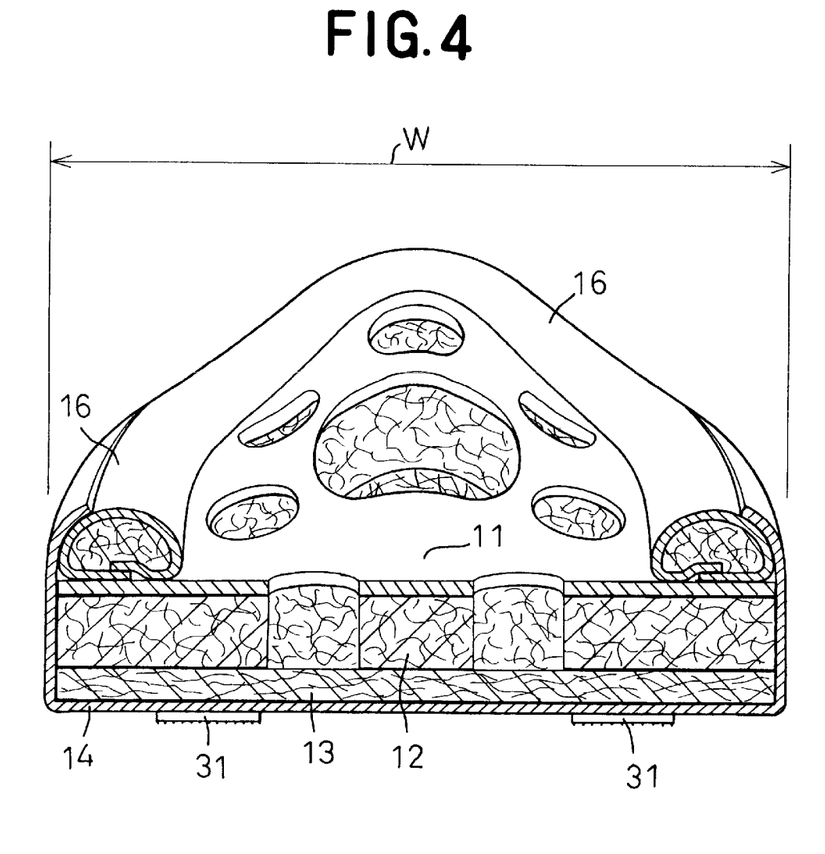
FIG. 4 is a sectional view taken along line B—B in FIG. 2.

FIGS. 2–4 show the pad 1 respectively in a perspective view, a sectional view taken along its longitudinal axis A—A bisecting its width W and a sectional view taken along its transverse axis B—B orthogonal to the longitudinal axis and substantially bisecting its length L into a front region 3 and a rear region 4. The pad 1 is contoured by a longitudinally front edge 6, a longitudinally rear edge 7 and transversely opposite side edges 8, 8 extending between the front and rear edges 6, 7. The pad 1 has a width W as measured between the transversely opposite side edges 8, 8 which is substantially uniform in the rear region 4 and progressively reduced from its zone adjacent the rear region 4 toward the front edge 6 in the front region 3 of the pad 1.

The pad 1 is a laminate comprising a top layer 11 destined to contact a wearer's skin, a feces holding layer 12 directly underlying the top layer 11, a moisture absorbent layer 13 directly underlying the holding layer 12 and a back layer 14 covering the lower surface of the absorbent layer 13. The pad 1 is formed on the upper surface of the top layer 11 with a leakage barrier 16 extending along the transversely opposite side edges 8, 8. Sections of the leakage barrier 16 progressively come nearer to each other until they are joined together at the front edge 6. The back layer 14 is curved upward in the vicinity of a front edge of the absorbent layer 13 so as to cover respective lateral surfaces of the top layer 11, the holding layer 12 and the absorbent layer 13 and finally to be joined to the outer surface of the leakage barrier 16.

As will be apparently understood from FIGS. 2–4, the top layer 11 is formed with at least one, preferably two or more through-holes 21. Each of these through-holes 21 has an opening area of 20–5000 mm$^2$ and the transversely middle one 21A of these through-holes 21 destined to be aligned with the wearer's anus may be dimensioned to be larger than the remaining through-holes 21. The holding layer 12 is formed immediately under the respective through-holes 21 with hollows 22 each having its opening area dimensioned to be equal to or larger than the opening area of the through-hole 21 immediately overlying this hollow 22. The hollows 22 are preferably provided in the form of through-holes extending through the holding layer 21 completely from upper to lower surfaces thereof. Referring to FIG. 2, the absorbent layer 13 is partially exposed within such through-holes (i.e., the hollows 22) and the hollow 22A immediately under the larger through-hole 21A has its opening area substantially corresponding to the opening area of the larger through-hole 21A.

As will be apparently understood from FIGS. 3 and 4, the top layer 11 and the holding layer 12 are placed one upon another wherein the lower surface of the former is joined to the upper surface of the latter by means of hot melt adhesive agent (not shown). In the rear region 4 of the pad 1, the assembly flatly extends and, in the front region 3 of the pad 1, the assembly curves upward with the top layer 11 inside. In the rear region 4, the absorbent layer 13 also horizontally extends and, in the front region, the absorbent layer 13 gently curves or bends upward in its transversely middle zone so that the assembly may be progressively spaced from said absorbent layer 13. In other words, the holding layer 12 and the absorbent layer 13 are joined together along the front and rear edges 6, 7 of the pad 1 but their curved portions cooperate with each other to form a vacant space 23 therebetween. The large through-hole 22A of the holding layer 12 communicates with this vacant space 23. The leakage barrier 16 joined to the upper surface of the top layer 11 horizontally extends in the rear region 4 and curves in the front region 3 like the top layer 11. The back layer 14 covers the lower surface of the absorbent layer 13 and extends outward sufficiently to cover the respective lateral surfaces of the top layer 11, the holding layer 12 and the absorbent layer 13. Outer edges of the back layer 14 are joined to the lateral surface of the leakage barrier 16 along the front edge 6 and the transversely opposite side edges 8 of the pad 1, on one hand, and joined to the upper surface of the top layer 11 along the rear edge 7 of the pad 1. Such back layer 14 may be joined to the lower surface of the absorbent layer 13 and/or the lateral surfaces of the respective layers 11~13, if it is necessary.

Figure 5:
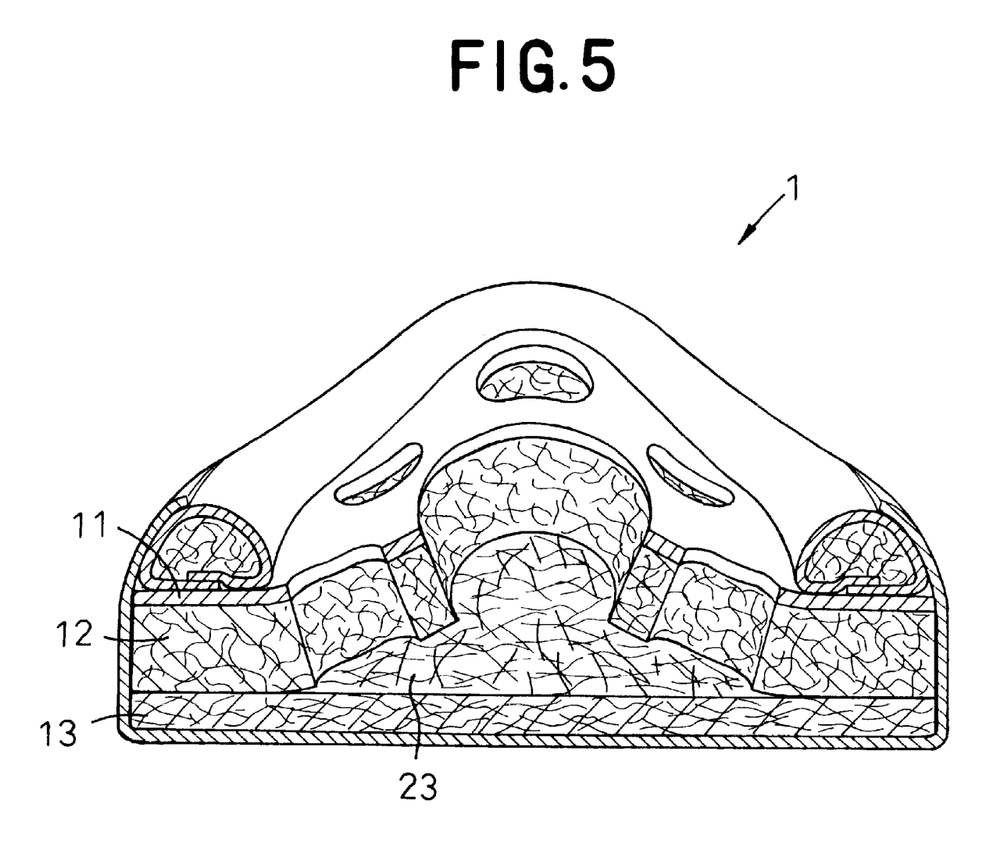
FIG. 5 is a sectional view taken along line C—C in FIG. 2.

FIG. 5 is sectional view taken along line C—C in FIG. 2. In the front region 3 of the pad 1, the top layer 11 and the holding layer 12 assembled together present an inverted V-shape as viewed in the transverse section of the pad 1 and the absorbent layer 13 is flat so that the vacant space 23 is formed between the holding layer 12 and the absorbent layer 13. The holding layer 12 and the absorbent layer 13 are placed one upon another and bonded together along their side edges. The top layer 11 or the assembly of the top layer 11 and the holding layer 12 may present the inverted V-shaped section not only in the front region 3 but also in the rear region 4 of the pad 1. With the top layer 11 of such configuration, the apex of the inverted V-shape fits into a groove of wearer's hip and effectively blocks a stream of loose passage flowing along this groove.

As suitable material for the top layer of the pad 1 according to this invention, hydrophobic sheet such as a nonwoven fabric of synthetic fiber, a synthetic resin film or a foamed sheet of synthetic resin may be used. The foamed sheet of synthetic resin is preferably a foamed polyethylene sheet, a foamed polystyrene sheet or the like having a basis weight of 25~80 g/m², a thickness of 0.5~3 mm and a density of 0.008–0.03 g/cm³. These sheet materials may have their top surfaces may be subjected to water repellent finish before their use.

The holding layer 12 may be formed by a three-dimensional network structure of synthetic resin having breathability and moisture-permeability in the thickness direction as well as in the transverse direction of the pad 1. As an example of such structure, a conjugated fiber of 6~100 deniers comprising polyethylene as a sheath and polypropyrene or polyester as a core joined together preferably in crimped condition so as to realize a basis weight of 100–1500 g/m² and a thickness of 5–100 mm. In such structure, 40 w/w %, preferably 30 w/w % of the conjugated fiber may be replaced by hydrophilic or water-absorbent fiber or fibrous highly water-absorptive polymer. This fibrous highly water-absorptive polymer may be heat-sealed with the conjugated fiber to form a part of the network structure. Foamed polyurethane of open cell type also may be used as the network structure. Preferably, these network structures are elastics exhibiting an elastic recovery of 50% or higher with respect to its initial thickness when a load of 35 g/cm² is exerted on the structure in its thickness direction for 5 minutes, then the structure is unloaded and left as it is for 30 minutes.

The absorbent layer 13 has a basis weight of 20–600 g/m² and an absorptivity of 8 g/g for physiological saline. This layer 13 may be formed by fluffy pulp, a mixture of fluffy pulp and highly water absorptive polymer particles or a mixture of thermoplastic synthetic fiber and fibrous highly water absorptive polymer. The last-mentioned mixture of thermoplastic synthetic fiber and fibrous highly water absorptive polymer may contain the fibrous highly water absorptive polymer of 70 w/w %. The thermoplastic synthetic fiber may be of hydrophilic nature or of hydrophobic nature. It should be understood that the thermoplastic synthetic fiber preferably is conjugated fiber crimped so that the absorbent layer 13 may be formed with a plurality of liquid-permeable vacant spaces and easily recover a thickness substantially equal to its initial thickness even after this layer 13 has been compressed in its moistened condition.

The back layer 14 may be substantially formed by a liquid-impervious or liquid-impervious but breathable non-woven fabric of synthetic fiber or film of synthetic resin. In the case of the synthetic resin film, its outer surface may be laminated with suitable nonwoven fabric to impart the back layer 14 a cloth-like touch.

The leakage barrier 16 comprises an assembly of crimped conjugated fiber or foamed synthetic resin such as spongy urethane covered with hydrophobic or substantially liquid-impervious nonwoven fabric or film and, in any case, the barrier 16 is elastically deformable under a compressive force. The illustrated embodiment of the leakage barrier 16 is substantially semicircular or elliptical in its cross-section (See FIGS. 3 and 4). This barrier 16 preferably has a width p of 5~30 mm and a height q of 5~20 mm. Configuration and dimension of the barrier 16 are not limited to those of the embodiment as illustrated and, for example, the barrier 16 may include its additional section transversely extending along the rear edge 7 of the pad 1, if it is desired.

Bonding the respective layers 11~14 of the pad 1 and the leakage barrier 16 one to another may be carried out using suitable adhesive agent such as hot melt adhesive agent or by heat- or ultrasonic-sealing two or more of these component one with another. The back layer 14 of the pad 1 may be provided on its lower surface with a hook member 31 (See FIG. 3) making a part of the mechanical fastener well known under the trade name of MAGIC TAPE or the like to fasten the pad 1 to the inner surface of the shorts 2 to be put on the wearer's body together with the pad 1. Preferably, only the rear regions 4 of the pad 1 is fastened to the shorts 2 and the front region 3 thereof is left free.

Having been put on the wearer's body, the pad 1 is positioned relatively to the wearer's body as shown by FIG. 1. The front region 3 occupies a relatively low position and the rear region 4 occupies a relatively high position on the wearer's body. The rear region 4 is placed on the wearer's hip with the larger through-hole 21A of the top layer 11 being substantially aligned with the wearer's anus. In this manner, the pad 1 inclusive of the rear region 4 is pressed and held by the wearer's garment such as the shorts 2 or diaper against the wearer's body. The front edge 6 of the pad 1 which is more or less tapered is received between the wearer's thighs or into the hip groove, on one hand, and the leakage barrier 16 is pressed against the wearer's hip, on the other hand, to prevent any amount of feces discharged onto the pad 1 from leaking from the pad 1. The leakage barrier 16 is elastically deformable under a compressive force to be maintained in close contact with the wearer's hip and thereby to ensure the leakage preventing effect even when liquid-rich loose passage has bee discharged on the pad 1. Within the pad 1, feces is guided through the through-holes 21 of the top layer 11 into the hollows 22 of the holding layer 12 and/or the vacant spaces 23 defined between the holding layer 12 and the absorbent layer 13. In this manner, the feces is reliably prevented from coming in contact with the wearer's skin. A moisture-content of such feces received in the hollows 22 and the vacant spaces 23 is absorbed by the fibrous highly water-absorptive polymer and by the absorbent layer 13, leaving solid content of the feces in the hollows 23 and vacant spaces 23. Use of a hydrophobic sheet as the top layer 11 is advantageous in that the moisture content of feces, particularly of the loose passage discharged onto the top layer 11 is repelled by the top layer 11 and easily guided into the hollows 22.

The pad 1 can hold the feces in the hollows 22 as well as the vacant spaces 23 and thereby kept the feces from contact with the wearer's skin in the manner as has been described above. Thus, the wearer's skin is reliably protect from being stained with the feces over a wide range and having a rash due to this. The solid content of the feces discharged onto the pad 1 can be taken out from the pad 1 and then disposed of into water closet. When it is desired to use the pad 1 in conjunction with disposable diaper, the latter may be of the type substantially adapted to deal with urine only, since there is few apprehension that the diaper might be soiled with the feces. The diaper to be used in conjunction with the pad 1 for such application may be of correspondingly simplified construction and may be made at a correspondingly low cost.

Figure 6:
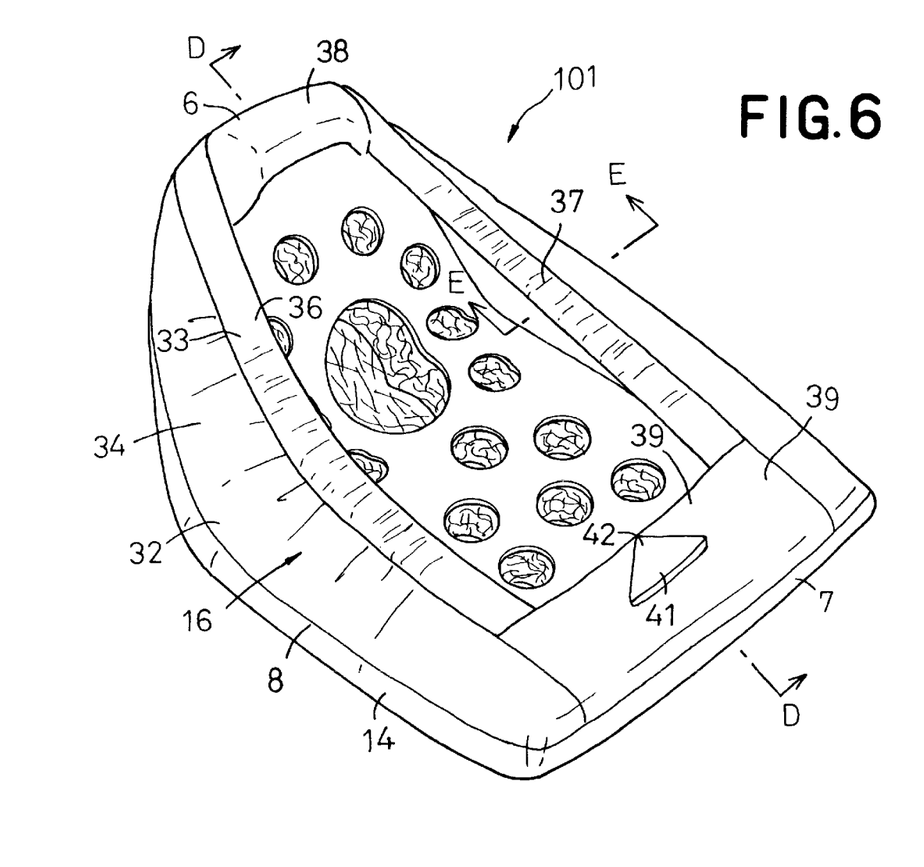
FIG. 6 is a view similar to FIG. 2 but showing one embodiment of this invention.
Figure 7:
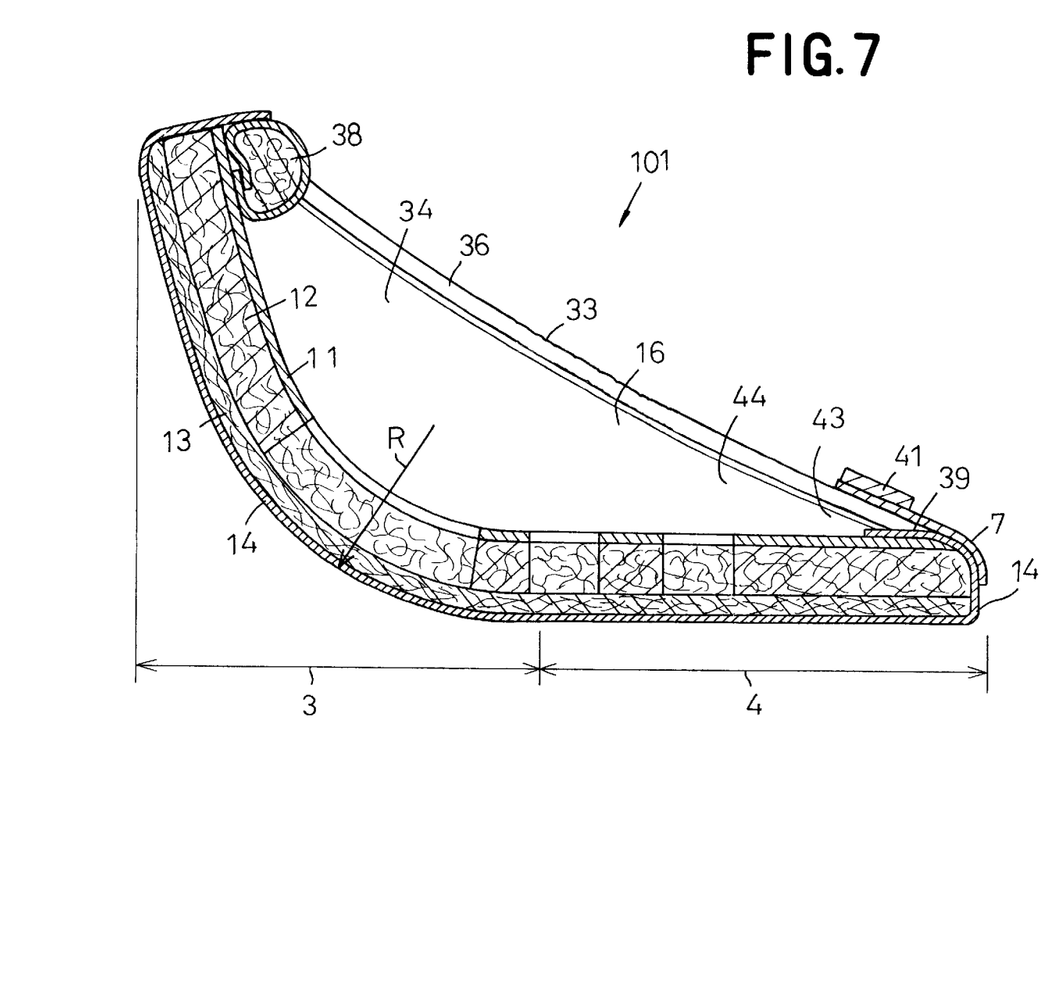
FIG. 7 is a sectional view taken along line D—D in FIG. 6.
Figure 8:
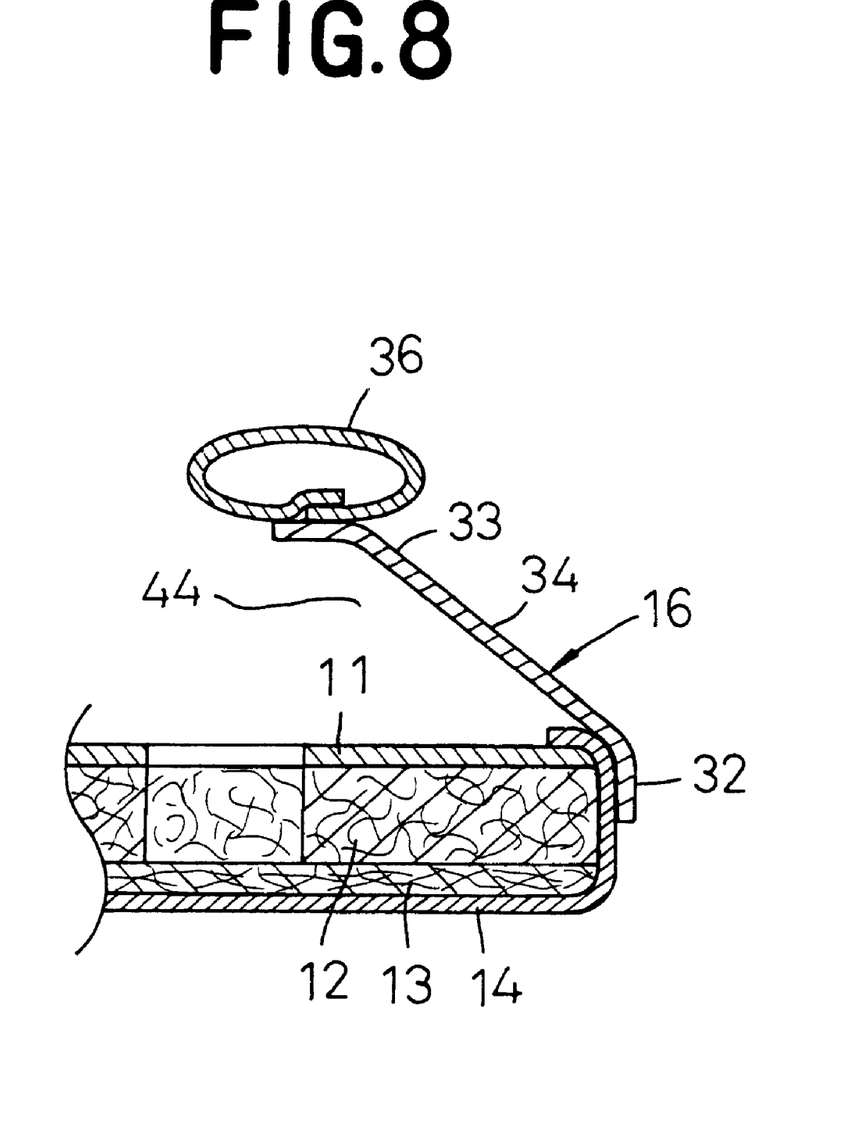
FIG. 8 is a sectional view taken along line E—E in FIG. 6.

FIGS. 6–8 are respectively a view similar to FIG. 2 but showing one preferred embodiment of this invention, a sectional view taken along line D—D in FIG. 6, and a sectional view taken along line E—E in FIG. 6. The pad 101 according to this embodiment is distinguished from the pad 1 of FIG. 2 in that there are provided a pair of relatively high leakage barriers 16 having an elastic stretchability in the longitudinal axis of the pad 101 bisecting a width of the pad 101. Each of the leakage barriers 16 substantially comprises a liquid-impervious sheet formed, for example, by a nonwoven fabric or synthetic resin film. Specifically, the leakage barrier 16 includes a proximal edge 32 placed upon the back layer 14 along, the transversely opposite side edges 8 of the pad 101, a top edge 33 lying above the upper surface of the top layer 11 and a side wall (i.e., leakage wall) 34 extending between the proximal edge 32 and the top edge 33. An elastic sheet 36 is rolled up in tubular shape and stretched in the direction of the longitudinal axis D—D until flattened. This flattened elastic sheet 36 is attached to the top edge 33. Gathers 37 are formed on said top edge 33 as the elastic sheet 36 contracts. The front edge 6 of the pad 101 is provided in its transversely middle with an elastic member 38 adapted to be received in the hip groove and thereby to block loose passage flowing along this groove. Along the rear edge 7 of the pad 101, a leakage sheet 39 extends between the pair of leakage barriers 16. The leakage sheet 39 is provided on a point at which the sheet 39 intersects the longitudinal axis D—D with an elastic member 41 so that a gap defined between the pad 101 and a recess along the wearer's backbone may be filled with the elastic member 41. The member 41 preferably has an equilateral triangular shape as viewed in its plan view, which is pointed toward the front edge 6, or can be pointed rearward. The elastic members 38, 41 are formed by an assembly of crimped conjugated fiber, foamed polyethylene sheet or foamed polyurethane and convex with respect to the transversely opposite side edges of these members. The leakage sheet 39 is joined not only to the top edges 33 of the respective leakage barriers 16 but also to the back layer 14 along the rear edge 7 of the pad 1 so as to form a first pocket 43 opening toward the front edge 6 of the pad 1.

As will be apparent from FIG. 7, the top layer 11, the holding layer 12 and the absorbent layer 13 are placed one upon another and joined together by means of, for example, hot melt adhesive agent (not shown). Between the holding layer 12 and the absorbent layer 13, the vacant space 23 of FIG. 3 is not formed. The front region 3 of the pad 101 describes a circular arc smaller than that in FIG. 3, for example, R=20~80 mm. This circular arc-shaped curve is maintained by the elastic member 36 being biased to contract.

Such pad 101 is put on the wearer's body with the elastic sheets 36 extending along the top edges 33 of the respective leakage barriers 16 placed in close contact with the wearer's skin over a range as a large as possible. The pad 101 has a second pocket 44 (See FIG. 7) defined between the upper surfaces of the top layer 11 and the inner surfaces of the respective leakage barriers 16 so that a sideways leak of loose passage can be reliably blocked and much amount of feces can be received between the pair of leakage barriers 16. Furthermore, the pad 101 is completely surrounded by the elastic members 38 and the first and second pockets 43, and 44. Such an arrangement also is effective to receive much amount of feces without an apprehension of its leakage.

Though not illustrated, this invention can be exploited in a manner such that the pad 1 or 101 is inseparably fixed to the diaper.

The article according to this invention has the relatively narrow front edge adapted to be received into a hip groove and the transversely opposite side edges formed with the elastically deformable leakage barrier(s) adapted to come in close contact with the wearer's skin. Such a unique arrangement enables the feces, particularly the loose passage to be received into the hollows and thereby protects the wearer's skin against being stained with the loose passage over a large range. The liquid-content of the loose passage received into the hollows is absorbed by the holding layer and the absorbent layer, leaving the solid-content in the hollows. With an advantageous consequence, the liquid-content causes no rash or eruption and the solid-content of the feces can be easily disposed of into the water closet. Use of the article according to this invention in conjunction with the diaper allows said diaper to have a function only to absorb the urine. In this may, construction of the diaper can be simplified and a cost required to make such diaper can be correspondingly reduced.

The laminate constituting the article according to this invention is put on the wearer's body with the front region of the laminate being curved with the top layer inside so that the article presents the J- or L-shape as viewed in its side view. Such J- or L-shape allows the article to be easily placed in close contact with the wearer's hip.

What is claimed is:

1. A disposable article for dealing with feces, having a longitudinal axis and a transverse axis orthogonal to said longitudinal axis, comprising: and
   a front region, a rear region adjoining said front region in a direction defined by said longitudinal axis and a feces receiving region formed symmetrically about said longitudinal axis; and
   said feces receiving region being provided in the form of a laminate that includes
      a top layer formed with at least one opening having an area of 20–5000 mm$^2$,
      a feces holding layer in the form of a three-dimensional structure underlying said top layer and formed with a hollow immediately under said opening of said top layer and having an opening area substantially corresponding to said area of said opening formed in said top layer,
      a liquid-absorbent layer underlying said holding layer and containing liquid-absorbent material of at least 50 w/w % and
      a liquid-impervious back layer covers a lower surface of said absorbent layer,
   wherein said rear region is formed to have a substantially uniform dimension in a direction defined by said transverse axis while said front region is formed to be tapered toward a front edge of said laminate and said top layer is provided on an upper surface thereof with a leakage barrier continuously extending along transversely opposite side edges of said top layer across said front and rear regions and wherein said leakage barrier is normally biased to rise on said top layer but elastically deformable in the opposed direction.

2. The article according to claim 1, wherein said top layer is formed by hydrophobic sheet material.

3. The article according to claim 1, wherein said laminate is substantially flat in said rear region and curved in said front region with said top layer inside as viewed from the side.

4. The article according to claim 1, wherein said leakage barrier is formed by crimped conjugated fiber or foamed synthetic resin.

5. The article according to claim 1, wherein said leakage barrier comprises a proximal edge being integral with said back layer along said transversely opposite side edges of said laminate extending across said front and rear regions, a top edge lying above the upper surface of said top layer and being elastically stretchable in said direction defined by said longitudinal axis, and a leakage wall defined by a liquid-impervious sheet extending between said proximal edge and said top edge.

6. The article according to claim 1, wherein there is provided, above transversely middle zone(s) of front and/or rear edge(s) of said laminate, a member adapted to be elastically compressible in a direction of the laminate's thickness and wherein said member is shaped to be convex with respect to transversely opposite ends thereof.

7. The article according to claim 1, wherein said holding layer has a thickness of at least 5 mm and said hollow immediately underlying said opening has a depth of at least 2.5 mm.

8. The article according to claim 1, wherein said hollow is provided in the form of a through-hole extending through said holding layer in a direction of its thickness.

9. The article according to claim 1, wherein at least one of said top layer and said holding layer presents an inverted V-shaped cross-section at least in said front region.

10. The article according to claim 9, wherein the front region of said holding layer presenting said inverted V-shaped cross-section has its transversely middle zone spaced from said absorbent layer.

* * * * *